(12) United States Patent
McGee (10) Patent No.: US 6,312,467 B1
(45) Date of Patent: Nov. 6, 2001

(54) METHOD OF RESTRUCTURING BONE

(75) Inventor: Thomas D. McGee, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 09/146,333

(22) Filed: Sep. 2, 1998

Related U.S. Application Data

(63) Continuation of application No. 08/682,150, filed on Jul. 17, 1996, now abandoned
(60) Provisional application No. 60/001,481, filed on Jul. 18, 1995, and provisional application No. 60/003,407, filed on Sep. 8, 1995.

(51) Int. Cl.$^7$ ...................................................... A61F 2/28
(52) U.S. Cl. ........................................................ 623/16.11
(58) Field of Search ............................. 623/16.11, 23.48, 623/23.49, 23.5, 23.51, 23.56, 23.57, 23.61; 606/62, 63, 67, 69, 72

(56) References Cited

U.S. PATENT DOCUMENTS

| | | | |
|---|---|---|---|
| Re. 33,161 | 2/1990 | Brown et al. | 423/308 |
| Re. 33,221 | 5/1990 | Brown et al. | 423/308 |
| 3,710,789 | 1/1973 | Ersek | 423/308 |
| 3,787,900 | 1/1974 | McGee . | |
| 3,849,805 | 11/1974 | Leake et al. . | |
| 3,906,550 | 9/1975 | Rostoker et al. . | |
| 4,938,768 | 7/1990 | Wu | 623/16 |
| 4,960,426 | 10/1990 | Atsumi . | |
| 5,112,354 | 5/1992 | Sires . | |
| 5,147,361 | 9/1992 | Ojima et al. . | |
| 5,211,661 | 5/1993 | Shinjou et al. | 623/16 |
| 5,211,664 | 5/1993 | Tepic et al. | 623/16 |
| 5,281,226 | 1/1994 | Davydov et al. . | |
| 5,443,483 | 8/1995 | Kirsch . | |
| 5,503,164 | 4/1996 | Friedman . | |
| 5,676,699 | 10/1997 | Gogolewski et al. . | |
| 5,693,099 | 12/1997 | Härle . | |

OTHER PUBLICATIONS

Thomas D. McGee et al., "A Biologically Active Ceramic Material With Enduring Strength", Encyclopedic Handbook of Biomaterials and Bioengineering, vol. 2, Part A (Materials), pp. 1413–1427.

Thomas D. McGee et al., "General Requirements for a Successful Orthopedic Implant", Encyclopedia Handbook of Biomaterials and Bioengineering, vol. 1, Part B (Applications), pp. 69–82.

Niederauer et al.; "Attachment of epithelial cells and fibroblasts to ceramic materials"; Biomaterials 1994 vol. 15, No. 5, pp. 343–352.

Tweden et al.; "Evaluation of the Tissue Response of Organic, Metallic, Ceramic and Osteoceramic Tooth Roots"; materials Science Forum vol. 293 (1999) pp. 17–36.

Thomas D. McGee et al.; "A Machinable Biologically–Active Composite as a Guide for Diaphysis Regeneration "; Presented at the International Symposium Advanced Materials for Orthopedic Applications, NIST, Jun. 8, 1999.

*Primary Examiner*—Michael J. Milano
(74) *Attorney, Agent, or Firm*—Dickstein Shapiro Morin & Oshinsky LLP (57) ABSTRACT

A method of producing reconstructed bone. The method includes providing an implant structure having a calcium phosphate component, and stabilizing the implant adjacent the healthy bone until tissue can recover, bond to the implant and support the normal required loading. The implant structure provides morphological continuity and anatomical contact between the implant body and the adjacent healthy bone. The method further includes providing for physiological processes to maintain a healthy junction between the implant and the healthy bone. The method further includes controlling, guiding and directing the bone reconstruction process in surgical situations where healthy recovery would not otherwise occur.

40 Claims, 3 Drawing Sheets

METHOD OF RESTRUCTURING BONE

CROSS-REFERENCES TO RELATED APPLICATIONS

This application is a continuation of U.S. application Ser. No. 08/682,150 filed on Jul. 17, 1996, now abandoned, which claims the benefit of U.S. Provisional Applications No. 60/001,481 filed Jul. 18, 1995 and No. 60/003,407 filed Sep. 8, 1995.

TECHNICAL FIELD

This invention relates to a method of producing restructured bone, and more particularly to a method causing bone to bond to an implant containing a calcium phosphate component, and a method to control the restructuring of bone through the use of an implant containing calcium phosphate.

BACKGROUND ART

The numbers in brackets below refer to publications listed in the Appendix, the teachings of which are incorporated herein by reference.

When viewed from an engineering perspective the human skeleton is a marvelous engineering structure. For the long bones, for example, the cartilage-covered epiphyseal surfaces of articulating joints cannot carry heavy stresses [1]. So the joints are enlarged to reduce that stress and provide smooth articulating surfaces with extremely low friction. These bearings are supported by a thin layer of dense bone supported by trabecular bone, with the trabecular bone aligned in accordance with Wolff's law to convey the low-stress bearing forces to the dense, high-stress cortical bone of the diaphysis [2]. This remarkable structure is even more remarkable because, during growth, the dense ring of diaphysis bone just below the growth plate is continuously elongated, with cartilage calcifying below the growth plate and chondrocytes building cartilage above, all without loss of strength as the process operates to elongate the bones [3]. In this process the cell differentiation, and the vascularization and ossification mechanisms, operate continuously to produce the dense bone of the diaphysis, and still maintain the large-area bearing surfaces. The stiffness of the diaphysis, with its dense cortical bone forming a tube, is much greater than that of a solid rod of the same mass. The exterior of the epiphysis is a structural membrane. From a mechanical point of view this is an example of a marvelous engineering structure.

The physiological process mentioned above can also be approached from an engineering point of view. It can be seen that, in each part of the structure there is a supply of cells, nutrients, enzymes, and chemicals to provide for growth, repair, and remodeling. Using the long bone joint as an example, provision for cellular activity is essential for growth, repair, and remodeling. For growth to take place there must be a steady supply of the necessary nutrients. Mechanisms for controlling that supply are extraordinarily complex [4]. For example, at the growth ring, formation of cartilage is inhibited by its own growth, causing differentiation of chondrocytes into osteoblasts. The perichondrium becomes a periosteum. The chondrocytes hypertrophy and die, producing a collagenous matrix containing cavities left by the empty chondrocyte lacunae. Osteoblasts line the cartilage and synthesize osteoid. The cartilage begins to calcify. This mineralization reduces diffusion of nutrients and the osseous tissue contracts, producing dense osseous tissue of smaller diameter, that of the diaphysis. The mechanisms are not understood. For example, the mechanism of precipitation of hydroxyapatite is unknown [5]. Transport of calcium and phosphate ions proceed separately. Nucleation may take place homogeneously in matrix vesicles, or heterogeneously at collagen fibril voids [6]. Regardless of the mechanisms and the complexities, however, this can be considered analogous to an engineering system, something like the logistics of battle support. The necessary nutrients, mechanisms, and other factors must be provided in a timely manner for the tissue to remain healthy and strong. This can include electrical transport, the effects of stress, and many other factors. In order to have a successful prosthesis, then, all aspects of skeletal engineering must be considered. Unfortunately this has not been done.

Orthopedic research can be divided into two areas, clinical and academic. Clinical research includes the improvements and modifications of existing prostheses and surgical procedures to improve patient care. Outstanding surgeons often work with prosthesis manufacturers to modify the existing practice in attempts to improve the performance [7]. Recently this has included the introduction of beads, mesh, and other structures on the surface of metallic implants to provide for tissue ingrowth and assist in stabilization [8]. Unfortunately, a roughened implant can also cause tissue irritation and lead to failure. New ideas, such as the substitution of pure titanium for the 6Al4V alloy, have been tested in the clinic. In the dental area, for example, two tooth-root prostheses made of carbon have been introduced into clinical practice and subsequently withdrawn because of failure [9, 10]. Thus the industry often is doing its research in the clinic.

Academic research is conducted through government laboratories, private laboratories, and academia. Here the research is highly specialized. Each individual specialty is dominated by the theory and practice of that specialty. For example, new materials are often evaluated on the basis of specific cellular responses to those materials regardless of whether the material is successful [11]. For example, carbon/Teflon mesh has been tested as an orthopedic material despite the fact that it is easily crushed in one's fingers [12]. Also, only after other countries adopted the idea of osseous integration was the Branemark titanium implant for tooth roots accepted in the United States. Before that time osseous integration was not considered grounds for acceptance.

The special nature of academic research has been allowed to dictate the research results. For example, bone and tissue interactions are often modeled by finite element methods to determine stress distributions in the prosthesis and in the bone [13]. But bone is complex. Almost all of these efforts have modeled bone as a continuum. In fact, bone is not isotropic and not homogeneous. Even today most finite element analyses are conducted assuming cortical bone has one set of homogeneous properties and cancellous bone has another set of homogeneous properties [14]. Actual bone varies tremendously, and the structure of the bone must be considered. When this is not done the results may be wrong and misleading. An even more serious criticism of this research is that the bone changes in response to the prosthesis. Where stresses are very high, bone is resorped, distributing the stress and changing the geometry. This is not modeled, so the model is inaccurate as soon as the implant is in place.

The political desires of research funding also strongly affect academic research. There is a large funded effort to study orthopedic materials in vitro, to avoid in vivo studies. Programs in cell attachment and other areas are funded despite the fact that the correlation of in vivo with in vitro has not been established [15].

The research method of academia is to divide and conquer; to study one variable while keeping all others constant. This advances fundamental knowledge but does not consider the interaction of various factors. Real orthopedic implants require the simultaneous application of chemistry, basic biological science, physiology, anatomy, materials science, stress analysis, and systems analysis. The bottom line is successful orthopedic performance. This requires synthesis from all pertinent areas, identification of the important and the trivial factors, experimentation, and decision making. This is the essence of engineering design.

Each year in the United States about 250,000 total hips replacement surgeries are performed. And about 25,000 hip prosthesis replacements are performed. The number of replacements is expected to climb because the life expectancy of a hip is 5 to 15 years. Patients are living longer. There is a need for improved hip prostheses.

Tissue response is critical to the success of an implant. It is the tissue response that determines the life of the implant because the hard tissue is continuously remodeling. Only if the tissue continues to support the implant can it be successful. The tissue response depends, in part, on the material from which it is made.

There are three classes of materials: metals, organic materials, and ceramics. The wrong material invokes classical undesirable tissue response. This includes inflammation, the presence of macrophages, a fluid-filled capsule, and resorption of surrounding tissue [16]. Most materials in all three classes invoke this response if they have any solubility in the tissue fluids. This puts serious limitations on the materials that can be considered. All the structural components of existing prostheses are selected to be bioinert [17]. These have minimum solubility. Metals such as titanium 316-L stainless steel, Al6V4 titanium, and cobalt-chrome alloys all are inert; although, especially in wear situations, some solubility and tissue reaction does occur. The organic polymers such as very high molecular weight (VHMW) polyethylene and polymethylmethracralate also are chosen for their minimum tissue response. Ceramic components such as alumina and zirconia are also bioiner. As such, all the inert materials are foreign bodies and are walled off by a thin fibrous capsule. The better materials have thinner capsules. However, there is not a direct bond of osseous tissue to bone. Such implants are only successful if the remaining tissue continues to support it. This will be time dependent because any movement of the prosthesis will increase the thickness of the fibrous capsule and because of the tissue degeneration described above, leading to more movement and progressive failure. The undesirable effects of electrochemical cells for electronic conductors such as metals and the degeneration of organics such as methacrylates and polyethylene would make the ceramic materials more attractive. Many ceramic compounds are highly insoluble and inert in a physiological environment, and most are electrical insulators. However, the ceramics are brittle. This limitation is discussed later.

Materials that are not inert but are not walled off by a foreign-body capsule have especially desirable tissue response. The only known materials of this nature are calcium phosphates. The ions released by the calcium phosphates, $Ca^{2+}$ and $(PO_4)^{3-}$ are also present in bone. The natural mineral in bone is impure hydroxyapatite, $Ca_{10}(PO_4)_6(OH)_2$, which contains water. Ceramic processes that require firing at high temperatures remove all or part of the water in hydroxyapatite. The residue may be oxyapatite of the same crystalline structure, or it may disproportionate into $Ca_3(PO_4)_2$ and $Ca_2P_2O_7$. Both are only slightly soluble and hydrolyze on the surface to hydroxyapatite. The tissue response for calcium-to-phosphorous ratios between 1.5 $[Ca_3(PO_4)_2]$ and 1.67 [hydroxyapatite] is known to be extremely compatible with hard tissue. Their performance is often call osteoconductive to distinguish it from osteoinductive, the latter being the production of osseous tissue in soft tissue sites. The lack of a fibrous capsule and the ability of bone to bond to the calcium phosphates makes them very interesting for prosthesis applications. Tissue response is critical, and if calcium phosphates can be used to achieve a bond between the implant and the hard tissue, they make long life a possibility. It is the tissue life that is so important. Therefore, to obtain improvement in tissue response to the current metals and alloys, the use of calcium phosphates is the only choice known at the present time.

An obvious approach to utilizing calcium phosphates, where they do not have the required strength, is to incorporate them into a composite. Combinations with plastics, metals, and ceramics can be considered. Composites based on plastics were rejected because it was difficult to expose the calcium phosphate when embedded in plastics. The limited rigidity was also a detriment. Composites based upon carbon were rejected for the same reasons, although fiber reinforcement was a desirable possibility. Composites based on metals were rejected because of reactions with the metals, including phosphorous embrittlement. High-temperature processing of metals alters the physical properties and requires reducing atmospheres, whereas the phosphates require oxidizing atmospheres. Therefore, ceramic-ceramic composites appear to be more promising.

Not many ceramic materials have no reaction with calcium phosphates at processing temperatures (up to 1500° C.). Based on physical chemistry and crystallographic considerations, magnesium aluminate spinel ($MgAl_2O_4$) was selected as a suitable second phase to use with a calcium phosphate [25, 26]. The ionic size of Mg is too small for extensive solid solution in calcium phosphates. The aluminum ion is too large to proxy for phosphorous. Spinel is an extremely stable compound, as are tricalcium phosphate and calcium pyrophosphate. Spinel is known to be an excellent, inert ceramic in its tissue response. If the calcium phosphate is to control tissue response, it must be distributed on a very fine scale. If it is not to cause large flaws, it also must be very fine grained. The calcium phosphate should not be easily leached away, so the calcium phosphate phase should be interconnected, not isolated. For this to occur the calcium phosphate phase should be at least 25 vol %. Fifty percent would be better.

Hip replacements are indicated when the femoral stem breaks off or when degenerative arthritis has made the joint too painful for function. Most of the procedures are performed for arthritis relief. The present design requires the removal of the ball and the stem of the femur. Removal of strong healthy bone to accommodate a femoral stem is undesirable and can be avoided with the design disclosed here. Excessive reaming of the acetabulum should also be avoided.

Part of the reason for attempting replacement of existing polyethylene and metal femoral components with inert hard ceramics, such as alumina, is to avoid wear and wear debris. Reduction in friction helps in this objective. However, the existing designs are only slightly modified from the conventional metal and polyethylene design, are subject to brittle failure (fracture of the stem, cup, etc.), are difficult to install and are expensive. The ball and stem must be machined in a very complex shape. And the balls and cups are the same shape and size as the polyethylene component. The size of the ball depends on the stresses that can be applied to the components.

All orthopedic implants currently in use rely on mechanical fixation, whether metal, ceramic, or plastic. Examples include: acetabular components and femoral components of a total hip, where screws and posts are used for fixation; knees where the femoral component is held with screws and the tibial component is held with posts and screws. All such implants are walled off by the foreign body response. A fibrous capsule wall separates the implant from the hard issue. Loosening under stress as the fibrous capsule deforms is progressive, because motion prevents repair and the capsule becomes thicker, which causes further loosening, etc. This is the most common mode of failure, usually after about five years.

The foreign body response is defined as the separation or walling-off of a foreign body such as an implant with a soft, fibrous, collagenous layer that prevents the hydroxyapatite of the bone from touching the implant. The fibrous capsule becomes thicker if there is motion between the implant and the bone. The thicker capsule allows more motion, which causes a still thicker layer. This is progressive and is the most common mechanism of failure for implants using mechanical fixation. Bone screws and other anchoring devices suffer from this encapsulation and is the reason a new method of fixation is needed.

The major cause of replacement is loosening under stress. Attempts to reduce this defect include hydroxyapatite coatings, beads or mesh for tissue ingrowth and modification of the alloys. Titanium and its alloys, 316-L stainless steel and cobalt chromium alloys are used for the femoral component. Both the acetabular and the femoral component are often cemented in place with polymethacrylate cement. The cement then has the tissue contact.

The cement is inserted under pressure before the prosthesis component is inserted. This ensures the cement fills the space between the prosthesis and the tissue. When the cement polymerizes the prosthesis is fixed, and forces applied to the prosthesis component are transmitted through the cement to the bone. However the cement, inserted under pressure into trabecular bone, penetrates and displaces the soft tissue in the trabeculae, effectively shutting off the blood and nutrient avenues for repair of the trabecular walls. Therefore, the area of heathy tissue contact is at the periphery of the cement. Degeneration within the cement cannot be repaired, and the bone at the periphery is in contact with whatever fracturing and internal debris produced in the zone adjacent to the periphery. This can cause the bone at the periphery also to degenerate.

The major cause for loosening is the foreign-body response of the tissue. All the plastics, conventional ceramics, and metals are walled-off with a fibrous capsule by the body's foreign-body response mechanism. If roughness or micro-motion occurs the capsule gets thicker, leading to more motion, more thickness and progressing to failure. Although the materials are chosen to be inert, to have a very thin capsule, this is the most common mechanism of failure.

Exiting total hip prostheses have a dense polyethylene cup and a metal femoral ball-and-stem design. Attempts are being made, especially in Europe, to replace both components with ceramic (alumina or zirconia.) In the United States they have not generally been accepted in clinical practice. Other than infection there are three principal causes of failure. One is the general deterioration by osteoporosis, a degenerative condition that is difficult to prevent. The second is wear of the polyethylene or metal components, that produces debris that causes tissue damage and dysfunction. The third is progressive loosening of the acetabular or femoral component, that leads to pain, dysfunction and failure.

When a tensile strain is applied to a natural hip joint the ligaments and muscles inhibit dislocation of the joint. One of the problems of the implants currently used is frequent dislocation.

The orthopedic surgeon is often faced with clinical situations in which bone has been removed, shattered or missing. Cancer surgery, accident trauma and genetic defects are frequently causes. Whenever this happens, and the remaining bone cannot be re-joined and stabilized in a satisfactory way, some sort of bone grafting is necessary.

The need for bone grafts is the result of natural limitations for bone to repair itself. In the event of fractured or missing bone the remaining bone must be stabilized in its natural position by internal or external fixing methods, such as internal or external bone plates and plaster casts. This keeps the bone from moving so that the physiology of bone repair can occur; typically hematoma, fibrous callous, mineralized callous and remodeling. However, if much fragmentation has occurred or if too much bone is missing the bone does not reunite even if the remaining bone is stabilized. This typical non-union problem is one reason for considering bone grafts. In some species, such as dogs and cats, for example, it is know that fractures of the diaphysis of long bones result in non-union whenever the length of missing bone is more than 1½ times the external diameter of the bone. Thus a method could be tested by grafting a longer defect in dogs and cats.

The best bone grafting material is natural bone, (autogenous bone) from somewhere else in the patient. This is used where practical. Unfortunately, it is often impractical because of the unavailability of suitable bone in the patient. Even when it can be obtained from the patient there is still the trauma of removal of bone from somewhere else in the body, the danger of fracture at the removal site, and the danger a second surgical procedure. Therefore, a source of bone grafts from some other source is essential in many clinical situations.

If autogenous bone is not available the surgeon often uses bone from the same species but a different individual in that species (allograft bone). This causes problems with the immune system and brings with it danger of infection. The success rate is lower than that of autogenous bone. Because of these risks a bone grafting method has long been sought for these difficult clinical situations. Much research has been conducted to find new materials to replace natural bone. This includes the full spectrum of biocompatible metals, organics (plastics) and ceramics. None of these has been successful because, in general, the inert materials chosen for the purpose are either walled off by the foreign body mechanism of the host (a fibrous capsule around the implant) or cause serious physiological responses when friction or chemical reactions produce particulates of the implant materials. Both causes are major sources of loosening of implants, pain and failure.

Many different devices and geometries of bone grafting have been attempted and many patents have been issued. Yet there is no standard material or method that can satisfy this common surgical problem. This is true because the problem is complex. It requires both material that is compatible with bone healing, restoration and remodeling mechanisms, and a way to utilize those mechanisms to repair the bone to its natural load-bearing state.

Those concerned with these and other problems recognize the need for an improved method of producing restructured bone and causing bone to bond to an implant.

DISCLOSURE OF THE INVENTION

The present invention provides a method of producing reconstructed bone. The method includes providing an implant structure having a calcium phosphate component, and stabilizing the implant adjacent the healthy bone until tissue can recover, bond to the implant and support the normal required loading. This invention also includes restructuring bone through the use of an implant having a calcium phosphate component in which the implant controls the anatomical features and physiological activity to produce restructured bone where the restructured bone would not occur if the implant were not used. When used as a load-bearing, enduring implant, the implant structure provides morphological continuity and anatomical contact between the implant body and the adjacent healthy bone. The implant geometry ensures the correct stress level, ensures mechanical stability, provides for local tissue bonding, and guides the reconstruction process. The method further includes providing for physiological processes to maintain a healthy junction between the implant and the healthy bone.

An object of the present invention is the provision of an improved method of producing reconstructed bone.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

The following examples are illustrative of the best mode for carrying out the invention. They are obviously not to be construed as limitative of the invention since various other embodiments can readily be evolved in view of the teachings provided herein.

EXAMPLE 1

There are at least five general requirements for a successful implant. These include tissue compatibility; sufficient strength and wear resistance for the application, including a low coefficient of friction where total joints are replaced; an adequate surgical procedure; provision for transfer of loads from the prosthesis to the tissue; and provision for the tissue to remodel, bond to, and support the tissue. Each of these is discussed separately.

A. Tissue Compatibility

Tissue response is critical to the success of an implant. It is the tissue response that determines the life of the implant because the hard tissue is continuously remodeling. Only if the tissue continues to support the implant can it be successful. The tissue response depends, in part, on the material from which it is made.

It is well known that calcium phosphates are not walled off by the foreign body response. However, they are brittle and often are mechanically weak. When used as plasma-sprayed coatings on other materials the coatings have weak adherence to the implant and can be resorbed because only thin coatings, typically 20 to 50 microns thick, can be applied. Attempts at using calcium phosphates in load-bearing situations have failed although wound healing and tissue contact are enhanced in the short term, up to three months.

Attempts to obtain tissue attachment often include porous bodies or bodies with surface porosity. It is known that the pores must be at least 200 microns in diameter to permit Haversian systems of blood supply to allow bone to grow into the pores. However, no applications exist where porous materials have healthy tissue attachment. Despite claims to the contrary, porous coatings such as metal beads or wire mesh on the surface of metals do not actually demonstrate tissue attachment, only tissue growth into cavities which then fails if stress is applied. There is a real need for actual tissue attachment to implants. Applicant has discovered how to make tissue attach to the implant, so that the tissue repairs itself and maintains the bond to the implant. This method is complex and is described as follows: To avoid the foreign body response so that the hard tissue in bone can bond to the implant it is necessary for the implant chemistry to be dominated by calcium phosphates such as tri-calcium phosphate, hydroxyapatite or fluorapatite. The calcium phosphate must be supported in some way so that the implant has enduring strength. One way to do this is to incorporate the calcium phosphate into a composite, where the second phase provides enduring strength and is too insoluble to alter the local chemistry at the implant to tissue interface.

Commercial tricalcium phosphate and commercial spinels were ball-milled together in water and an organic binder for 24 hours to produce a fine-grained mixture. They were filtered and dried to produce a cake. The cake was broken up and sieved to a free-flowing powder. The powder was pressed in a cylindrical mold at 400 psi and isostatically pressed at 25,000 psi. An axial hole was drilled and the tube was carved by hand to the desired geometry. Bars and pellets were also produced for property measurements.

Twenty bars were tested for cross-breaking strength to determine their tensile strength. One half of each are was tested after implanting them in the backs of dogs for 10 months. The other half was tested for comparison after the same time period. There was no statistical difference, indicating that the composite had enduring strength. This is logical because the calcium phosphate phase had the largest grain size and was the large flaw in the composite. The structure is like that of a sponge. The skeleton of the sponge is the inert spinet. The holes in the sponge are filled with calcium phosphate. The composite is called an osteoceramic.

Numerous tests of the osteoceramic show that bone bonds to it in the same way it does to tricalcium phosphate and hydroxyapatite. This satisfies the material requirements.

The McGee patent U.S. Pat. No. 3,787,900, disclosed such a composite, an osteoceramic. This patent is incorporated herein by reference.

This patent has now expired and no one has been able to use it despite its tissue compatibility.

The McGee patent describes a biologically active ceramic material containing calcium phosphate and an inert material such as spinel. It has excellent hard tissue compatibility. In fact, in Example II of the patent, tissue grew into the pores of an unloaded tooth root so well that it could not be extracted. The tooth root was entirely subgingiva, so was unloaded. Real prostheses must be loaded and tissue compatibility is not enough. The bone must be induced to reconstruct in such a way as to bond to the implant, and continue to do so indefinitely; or it must be induced with the aid of the implant to reconstruct itself enough to support the load. Applicant has discovered a method to cause the bone to reconstruct itself, either supporting an implant or being influenced by an implant to achieve a permanent skeletal repair. For this purpose a calcium phosphate material is essential. If the implant is to support the load, it must have enduring strength. The material described in the McGee patent is suitable for either result.

B. Strength and Wear Resistance

1. General Considerations

The contact of the tissue with an implant should not cause wear. Wear occurs at the articulating joints, where movement is mandatory. For most applications, then, strength is a critical element. Much research has been conducted on the strength of metal and plastic prosthesis materials. Because there are so few suitable metals that have reasonable tissue compatibility, the properties and the manipulation of the properties are well know [18]. Within the limitations of the properties, the geometry of the prosthesis must be selected to provide suitable strength.

There are two obvious strength limitations. One is that the strength of the implant must be sufficient to support the loads applied to it. The other is that the implant should be at least as strong as the bone. Load-bearing orthopedic implants often are anchored in dense bone so the latter limitation require a minimum tensile strength of about 140 MPa to match the strength of the bone [19]. Within this limitation, because bone geometries support the load, it should be possible to design implants that also will support the load.

Metals have much higher strength and higher modulus of elasticity than bone. This makes manipulation of the geometry to support the load relatively easy. However, the high modulus of elasticity can cause stress concentration in the presence of shear stresses. (A simple compressive stress does not cause stress concentration if the Poisson component of the strain can be accommodated.) Where "stress shielding" has been identified as a failure mode (plates and femoral components), the interface is in shear. This experience tells us that the implant design is best if shear situations are minimized. However, because requirements for tissue compatibility favor calcium phosphate ceramics, we need to examine them carefully. Calcium phosphates are not hard; they would not be used for articulatory bearing surfaces. Hard, inert ceramics have superior wear resistance. Metal on polyethylene wears 50 $mm^3$ per year, but polycrystalline alumina on polycrystalline alumina wears only 0.01 to 0.02 $mm^3$ per year, a factor of $\frac{1}{2000}$ to $\frac{1}{5000}$ better [20]. Obviously, if wear is important, ceramic materials have great prospects.

2. Strength of Calcium Phosphate Ceramics

Two calcium phosphates—tricalcium phosphate, $Ca_3(PO_4)_2$; and hydroxyapatite $Ca_{10}(PO_4)_6(OH)_2$—have been extensively studied for tissue compatibility [21]. Because of their excellent tissue response they are now being used in granular and block form for orthopedic repair. Successful use in load-bearing situations has not been reported. Fatigue failure occurs even when prestressed, dense hydroxyapatite is used [22]. This is to be expected because of the brittle nature of calcium phosphates. This is also true of various bioglasses and glass ceramics that react with tissue because the very fact of reactivity introduces weakness. Thus calcium phosphates, by themselves and in bioglasses, can be expected to fail under functional loads.

Calcium phosphate coatings, plasma-sprayed on the surface of metals or ceramics, have similar weakness. Although wound healing may be enhanced by the presence of calcium phosphates, the bond between the calcium phosphate and the substrate is only mechanical. Thick coatings fracture off spontaneously, so only a few microns can be applied, typically 20–40 microns. This is easily removed by the tissue. Osteoclasts dissolve readily both tricalcium phosphate and hydroxyapatite. Before proposing a solution to this problem, let us consider the reasons for the weakness.

In common with almost all ceramics the calcium phosphates are brittle materials. They have no ductile or plastic deformation mechanisms. So the presence of a surface flaw causes severe stress concentration that cannot be relieved by plastic or ductile flow. The strength, then, depends on the manufacturing process. The calcium phosphates are never completely dense. They have some porosity. This reduces the strength [23]. When large pores are introduced deliberately to enhance tissue ingrowth, they seriously weaken the material. The pores serve as flaws. Although their shape is important, the strength is inversely proportional to the square root of the pore size. Even small pores cause weakness. If a calcium phosphate implant, or a bioglass implant, is modified by host dissolution, then the strength is reduced because flaws are introduced. This is a fatal limitation for such materials in load-bearing applications [24].

Ceramic materials fail in tension because of the effect of the flaws. Typically they are 10 times stronger in compression than in tension. And when stressed to the ultimate in compression, they fail in shear. Obviously, loading them in compression, and prestressing them in compression, will help prevent failure.

Many attempts have been made to produce flaw-free ceramics. The best polycrystalline alumina hip components are the state of the art in obtaining high strength. And their insolubility helps preserve that strength. Unfortunately, the calcium phosphate ceramics cannot be made strong and retain that strength because of their most valuable feature, their solubility in the host. Some other way must be found, then, to take advantage of the biocompatibility of the calcium phosphates. Obviously, implants should never be attempted until after testing them in the host environment.

C. Surgical Procedure

The surgical procedure used to place an orthopedic implant is critical to the success. Recently, computer controlled machinery has been used in the operating room to improve the placement and alignment of prostheses. Of course, aseptic methods are required. Yet it is obvious that the skill and knowledge of the surgeon is critical to the success of the implant. The surgeon's skill in maintaining sterility, sectioning, alignment, torquing screws, and many other factors determines whether the implant has the possibility of success.

For existing prostheses the existing surgical procedures have serious deficiencies. The use of cement in trabecular bone shuts off the blood supply to the supporting bone. Removal of the ligament providing blood to the center of the femoral ball in a total hip procedure destroys the blood supply to supporting bone, especially medially. Removal or crushing of excess trabecular bone interferes with the blood supply in tibia tray replacement. These are known to be weak areas where failure often originates. The method disclosed here teaches how to avoid these errors in surgical procedure.

D. Provision for Transfer of Loads from the Prosthesis to the Tissue

Each type of implant must replace a functional orthopedic component. For that to occur, the loads imposed on the component must be known. In the case of a joint replacement the kinematics of the joint must also be known. Such loads are always dynamic. They may be suddenly applied and have a higher value than the static load. Many studies have been conducted on the kinematics and loads of the human skeleton. So the basic information is available. The difficult task is to devise a geometry for the implant that allows for load transfer to the tissue in such a way that the tissue will respond and support the prosthesis. Every application is different. The method will be illustrated with examples.

In all load-bearing prosthesis currently in use, the prosthesis is mechanically fixed to the bone. If that mechanical fixation is compromised by fibrous capsule movement, cellular deterioration from debris, excessive stress, loss of blood supply or for any other reason, the prosthesis will fail. Even in non-load-bearing situations; for example where hydroxyapatite granules are used to fill periodontal disease cavities, the tissue only surrounds the implant. Healthy bone is not induced to support the implant. My method of bone reconstruction teaches how to make the tissue support the implant through its natural physiological responses. The tissue remodels to maintain mechanical stabilization. This has never been achieved before.

If tissue is to bond to an implant the implant must be constructed so that the normal physiological response of the tissue for bone repair will function. This can be done by means of controlled implant surface geometry that provides for anatomical continuity and mechanical strength of the bone—so that the bone will repair itself, bond to the implant, and continue to maintain that bond using the conventional physiological responses of bone repair and maintenance.

Applicant has discovered that the means for bone to bond to an implant is that the surface of the implant should have a configuration so that the bone can have microstructural continuity with the implant. This is necessary so that the bone can build the same local structure it normally would if the implant were not there. For example the diaphysis of the femur is a dense tube with a certain wall thickness. The implant, then, must also be a dense tube with about the same wall thickness. The re-building bone will be dense bone so it will be able to accommodate support of the dense tube wall of the implant. This automatically puts the stresses the bone must support at the same level as it would have if bone were there instead of the implant. If the bone is trabecular bone then the surface of the implant must have a general microstructural configuration so that individual bone trabeculum can remodel and conform to the similar configuration on the surface of the implant. The microstructural features only need be deep enough on the surface to allow the bone to conform and support the local stresses delivered to the trabeculae. (The whole implant should not have that microstructural configuration because that weakens the implant.) This allows the tissue to have continuity of stress at the microstructural level of individual trabeculae at the interface.

By the term microstructural continuity reference is made to the hard tissue portion of the bone, that is, the portion that carries physical stress. In the case of trabecular bone, for example, it is the webs of the trabecula that carry the stress, not the soft tissue portion. (Hydrostatic stresses can exist within the trabecular soft tissue spaces and will continue after the wound healing is complete.) The point here is that the trabecular webs are normal anatomical features. The implant surface in trabecular bone should have the same web-like projections so that wound healing is caused to rebuild the trabecular bone to support the implant by attaching to the webs. Applicant has discovered the tissue will do this because the anatomical continuity provides physical stresses in the tissue that the tissue normally accommodates. From the tissue point of view this gives stresses in the same range that the hard bony part of the tissue would have if the implant were not there, but normal bone was. For cortical bone of the diaphysis the hard, load-bearing portion of the bone is somewhat tubular in shape. So the shape and cross sectional area of the implant should have basically the same shape and dimensions. Note that this requirement for microstructural continuity does not extend to the cellular level. Rather it is intermediate region between cellular and exterior geometry. It is the load-bearing portion of the bone that must have microstructural, or anatomical, continuity.

Applicant has discovered that the tissue can be induced to provide strength to the tissue-to-implant interface by means of macrogeometric features. The tissue will grow into large spaces to provide sufficient strength if the anatomical and physiological process can be maintained. This is possible when the anatomy, such as blood supply, is not blocked and the areas of bone in-growth or over growth are large enough to provide the type of normal, healthy bone normally present at the site.

This cannot be achieved by the microstructural continuity consideration above. Provisions must be made in each implant situation so that sufficient tissue strength is available for tension, compression, torsion, and bending stresses that can be imposed. This requirement must be satisfied by means of the macrogeometry of the implant. For example, a splined tube with projections of bone into the splines can accommodate torsional stresses. If the spline openings are tapered so that bone in-growth forms a key it can withstand tensile and bending forces. This requirement must be viewed from the tissue strength and physiological response point of view. It is not mechanical fixation in its usual sense. Rather it is tissue strength and viability under the imposed forces that must be provided. This requires an understanding of the tissue repair and remodeling processes, and the forces that the tissue must accommodate. Then the mechanical fixation to the implant is provided by the bone itself This will be explained further in the example below.

E. Provision for Tissue Remodeling

Once an implant is in place the natural physiological response of wound healing, callus formation, and remodeling must take place for the implant to be successful. This means that the geometry of the implant should not interfere with the transport processes and cellular responses required for repair. Most current implants are placed without regard for this principle. Crushing or drilling of cancellous bone through stem placement, injecting of cement, and removal of important supply routes, often occurs.

In most animals, the blood supply for cortical bone in the diaphysis is supplied by the medulla and the surrounding muscle. Bone repair is more rapid endosteally than periosteally. This means that the implant must also be a tube, so that the medulla can regenerate to supply blood and fluids to the wound-healing site. Then both the external and internal processes can operate normally.

As explained above, applicant has discovered that an additional requirement is that the physiological processes necessary for maintaining tissue bonded to bone must remain healthy after the implant is placed. This not only requires good surgical technique, but it also requires utilization of the anatomical features necessary for healthy physiological response. The blood supply and lymphatic service to the tissue must remain intact. This means that tissue projections into the implant must be large enough to be supported by the normal physiological processes. Note that this requirement is almost universally violated with existing prostheses. For example, the femoral stem of a total hip, supported with methacrylate cement, effectively blocks the medullary blood supply to the endosteum; and the ligaments and blood vessels attached to the femoral crown are removed, greatly inhibiting the blood supply to the cortical bone supporting the prosthesis.

All the above requirements are included in this method of making hard tissue attach to an orthopedic implant.

Based on the above considerations the details of the design can now be specified:

1. The chemistry of the host/implant reactions must be dominated by a calcium phosphate ceramic.

2. The implant should have a tensile strength at least as strong as the cortical bone it contacts. The strength should not depreciate in the host atmosphere.

3. The surgical procedure should be appropriate to the implant site, aseptic, without unnecessary trauma to the tissue, and provide temporary support for the implant.

4. The design of the implant should provide stress levels normal to the bone and allow for tensile, compressive, bending, and torsional loads. Shear stresses at the interface should be minimized.

5. The implant should not interfere with the normal internal and external processes associated with wound healing, recovery, and remodeling.

The following example discloses a method of making hard tissue bond to an implant, so that the implant is functional as the result of bone bonding, rather than mechanical fixation. Temporary fixation is, of course, required so that the wound healing and remodeling necessary for tissue bonding can take place. However, after bonding has taken place the temporary supports can be removed. The replacement of a section of a long bone is used here to discuss the principles involved. We will consider a "bone bridge" replacement of a section of a dog's femur.

The diaphysis of the femur of a dog is in the shape of a tube, slightly curved. The cortical bone of the tube is thin. The forces imposed on the tube are compressive, bending, tension, and rotation. Because of the offset neck of the femur, important bending forces put the tube in tension laterally and in compression medially. A prosthesis put into place must withstand these forces; but, more importantly, the bond of the tissue to the implant must also be strong enough to withstand these forces. The structure of the tissue implant interface must be adjusted to achieve this. When no implant is in place the continuous remodeling of mature bone, which is known to be stress regulated, maintains the tube shape and thickness. Any implant, then, should produce the same field of stresses as the natural bone. This dictates the nature of the contact between the bone and the implant. The resolved areas of contact for the implant should be the same as the area would be if bone were present instead of the implant. The structure of the implant in contact with the bone should encourage bone bonding.

Figure 1:
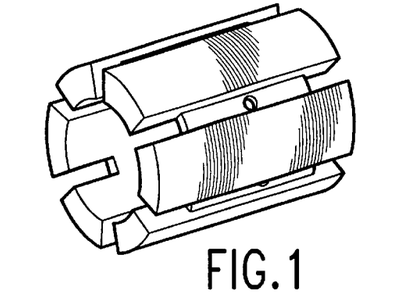
FIG. 1 is a perspective view of the bone bridge implant used in the method of the present invention.

A basic tubular shape was adopted to provide for normal healing. The wall thickness was the same as the cortical bone, so that the compressive stresses delivered to it would be the same as if the bone were continuous. (Several specimens were provided so that the surgeon could choose the appropriate one.) Tensile and torsional forces were accommodated by forming the end of the tube with dovetailed recesses so that bone could grow into the recess. After the recesses were filled the bone could not be withdrawn, providing tensile force accommodation. Torsional stresses were also accommodated by the bone grown into the recesses. After the recesses were filled bending stresses also could be accommodated. However, it is critical that the bone maintain the bond with the implant. This was encouraged by a series of axial grooves on the outside of the implant, with radial holes conducting blood from the medulla to the grooves (FIG. 1). The net result looks like a splined tube. It can accommodate tensile, compressive, bending, and torsional loads. It does not interfere with wound healing, callus formation, and remodeling. This satisfies the physical design requirements.

C. The Surgical Procedure

Anesthesia was induced with intravenous thiamylal sodium (17.5 mg/kg) and maintained with 1–3% halothane gas. Cephalothin sodium was administered pre and post surgical procedure as an antibiotic (20 mg/kg). The rear quarter of the dog was clipped and prepped using alternately Betadine and 95% alcohol. A 5-min sterile scrub with Betadine was performed following the initial preparation. The ECG was monitored. The leg was draped using aseptic technique and covered with a sterile stockingette.

Figure 2A:
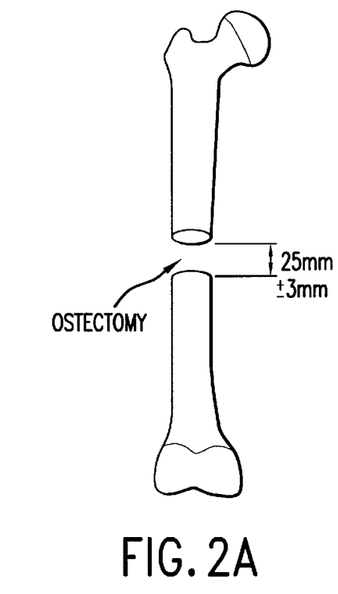
FIGS. 2A, 2B, and 2C are a series of front elevational views of a femur illustrating a surgical procedure used in the present invention.
Figure 2B:
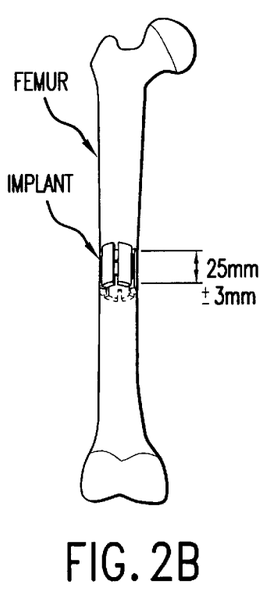

A skin incision was made along the cranial border of the biceps femoris muscle from the level of the greater trochanter to the proximal patella. The skin was sewn to the stockinette using 2/0 monofilament nylon. Electrocautery was used to help provide hemostasis. The skin margins were retracted and the fascia lata was incised along the cranial border of the biceps femoris muscle. The biceps femoris was retracted caudally and the vastus laterus muscle was retracted cranially to expose the shaft of the femur. An 8-hole 316 L stainless steel compression plate was contoured to the lateral aspect at the center of the femur for later use. A section of the adductor muscles, which insert on the caudal aspect of the femur, was elevated at middiaphysis. The vastus intermedius was retracted from the cranial aspect of the femur at the same level. Two transverse osteotomies were then made with an oscillating saw (FIG. 2A). Each was approximately 12 mm from the midshaft. The diameter and the length of the osteotomy were measured, and an implant was selected of the same length and cortex thickness (FIG. 2B).

Figure 2C:
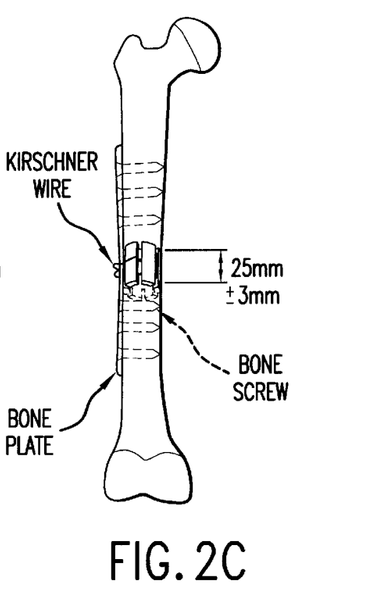

The implant was secured to the contoured plate with Kirschner wire (FIG. 2C). The plate was clamped to the lateral aspect of the femur to oppose the proximal and distal osteotomy sites to the ends of the implant. Three 3.5-mm cortical screws were placed on each side of the implant. The first screws on each side were aligned with a guide to produce compression of the bone to the implant. The area was irrigated with saline. The facia latera was closed with 0 monofilament polyglyconite sutures. The subcutaneous fat and fascia were closed with 2/0 monofilament nylon sutures. The skin was apposed with 4/0 surgical steel sutures. Cefadroxil (10 mg/kg per dose) was given twice a day for 6 days. The steel sutures were removed after 10 days.

The stainless steel compression plate was fixed to the proximal and distal bone plate. The compression of the bone to the ends of the plate brought the bone tightly to the ends of the implant, so that flexing of the plate would deliver compressive stresses to the ends of the implant. The bone plate was positioned laterally so that the normal bending stresses of load bearing would produce tension in the bone plate. This method of fixation satisfies the requirement that the implant be stabilized while wound healing and remodeling occur. Note that the movement that develops with time as the mechanical fixation of the bone plate deteriorates allows the bone to gradually accept the stresses imposed on the tissue/implant interface. The tissue remodels to accept the forces previously delivered to the bone plate.

The osteoceramic was formed as a dense tube with the same wall thickness and external (and internal) diameters as the cortical bone. This satisfies the important requirement that the implant should have microstructural continuity with the bone, and automatically assures that the stresses in the bone and in the implant are the same. The tissue remodels to support the implant in the normal range of stress that it would have if the implant were not present and bone was present instead.

The ends of the implant were provided with radial, tapered key-ways (FIG. 1). After bone grew into the keyways the taper prevented the keys from being withdrawn, providing tensile strength to the bone/implant assembly. Longitudinal grooves were provided so that bone could bridge completely across the implant lying in the grooves and contributing additional tensile and bending strength. Since bone remodels to accommodate stress the density and thickness of the bone at the root of the keyway and in the grooves could be adjusted by the tissue to maintain structural integrity. The compressive stresses were taken at the projected area of the tissue at the value normally present because the diameter and the thickness of the tube was the same as the cortical bone. Torsional stresses were accommodated by the same structure as described for tension. Thus, the implant geometry satisfies the requirement that the forces imposed can be accommodated by the tissue.

At mid-diaphysis the blood supply for bone remodeling is provided by vascularization of the medulla and from the surrounding muscles. These supply the endosteum and periosteum respectively. The medullar supply could regenerate through the axial hole of the implant. Both endosteum and periosteum had their normal blood supply so that the normal physiological responses could generate and maintain healthy bone in the key ways. Radial holes were also provided connecting the axial hole to the longitudinal grooves (FIG. 1). This provides blood supply to the bone in the grooves making it possible for the tensile tissue in the grooves to generate and remain healthy. These provisions satisfy the requirement that the physiological and anatomical processes can operate normally to provide for healthy attachment to the implant.

D. Results

This procedure produced an implant that was in compression at the ends, the bone plate taking the tension forces in bending and pulling. After wound healing took place the bone began to attach to the implant. The bone plate provides a resistance to bending loads. The edges of the bone plate, held tightly against the periosteum by the bone screws, cut through the periosteum and interfered with the external blood flow at that location, producing a weaker bone under the bone plate. The bone plate and the bone screws are walled off by the foreign-body capsule in such a way that movement becomes possible with time. The compressive and tensile loads gradually shift to the implant as the tissue responds to the stress stimulus, gradually taking more of the load. This can be observed radiographically as the bone fills the dovetail recesses and the longitudinal recesses. After about 1 year the bone plate was removed in a second surgical procedure. Enough stress had been transferred to the implant so that the bone plate was no longer necessary. The weak area under the plate was sufficiently local that fracture did not occur. The bone continued to remodel over 4 months. Four years after removal of the bone plate the dog was active, continuing to stress the implant normally without evidence of pain or gait variations. No further changes in remodeling occurred although it is believed the longitudinal recesses are completely filled with bone.

E. Conclusion

An orthopedic bone bridge has been designed in accordance with engineering design requirements to become a functional part of a living orthopedic system. By adhering to the requirements for (1) tissue compatibility, (2) strength, (3) surgical procedure, (4) load transfer to the living tissue, and (5) tissue remodeling, the bone bridge was made functional. It was necessary to control the tissue reaction to make the tissue form an enduring attachment. No previous implant has achieved this result. This is a successful orthopedic implant.

Existing implants violate some of the important features of the method presented here.

EXAMPLE 2

Existing total hip prostheses have a dense polyethylene cup and a metal femoral ball-and-stem design. Attempts are being made, especially in Europe, to replace both components with ceramic (alumina or zirconia.) In the United States they have not generally been accepted in clinical practice. Other than infection there are three principal causes of failure. One is the general deterioration by osteoporosis, a degenerative condition that is difficult to prevent. The second is wear of the polyethylene or metal components, that produces debris that causes tissue damage and dysfunction. The third is progressive loosening of the acetabular or femoral component, that leads to pain, dysfunction and failure.

Hip replacements are indicated when the femoral stem breaks off or when degenerative arthritis has made the joint too painful for function. Most of the procedures are performed for arthritis relief. The present design requires the removal of the ball and the stem of the femur. Removal of strong healthy bone to accommodate a femoral stem is undesirable and can be avoided with the design disclosed here. Excessive reaming of the acetabulum should also be avoided. The design disclosed here reduces that propensity.

Part of the reason for attempting replacement of existing polyethylene and metal femoral components with inert hard ceramics, such as alumina, is to avoid wear and wear debris. Reduction in friction helps in this objective. However, the existing designs are only slightly modified from the conventional metal and polyethylene design, are subject to brittle failure (fracture of the stem, cup, etc.), are difficult to install and are expensive. The ball and stem must be machined in a very complex shape. And the balls and cups are the same shape and size as the polyethylene component. The size of the ball depends on the stresses that can be applied to the components.

All orthopedic implants currently in use rely on mechanical fixation, whether metal, ceramic, or plastic. Examples include: acetabular components and femoral components of a total hip, where cements, screws and stems are used for fixation; knees where the femoral component is held with cements and screws and the tibial component is held with cements, posts and screws. All such implants are walled off by the foreign body response. A fibrous capsule wall separates the implant from the hard issue. Loosening under stress as the fibrous capsule deforms is progressive, because motion prevents repair and the capsule becomes thicker, which causes further loosening, etc. This is the most common mode of failure, usually after about five years.

Figure 3:
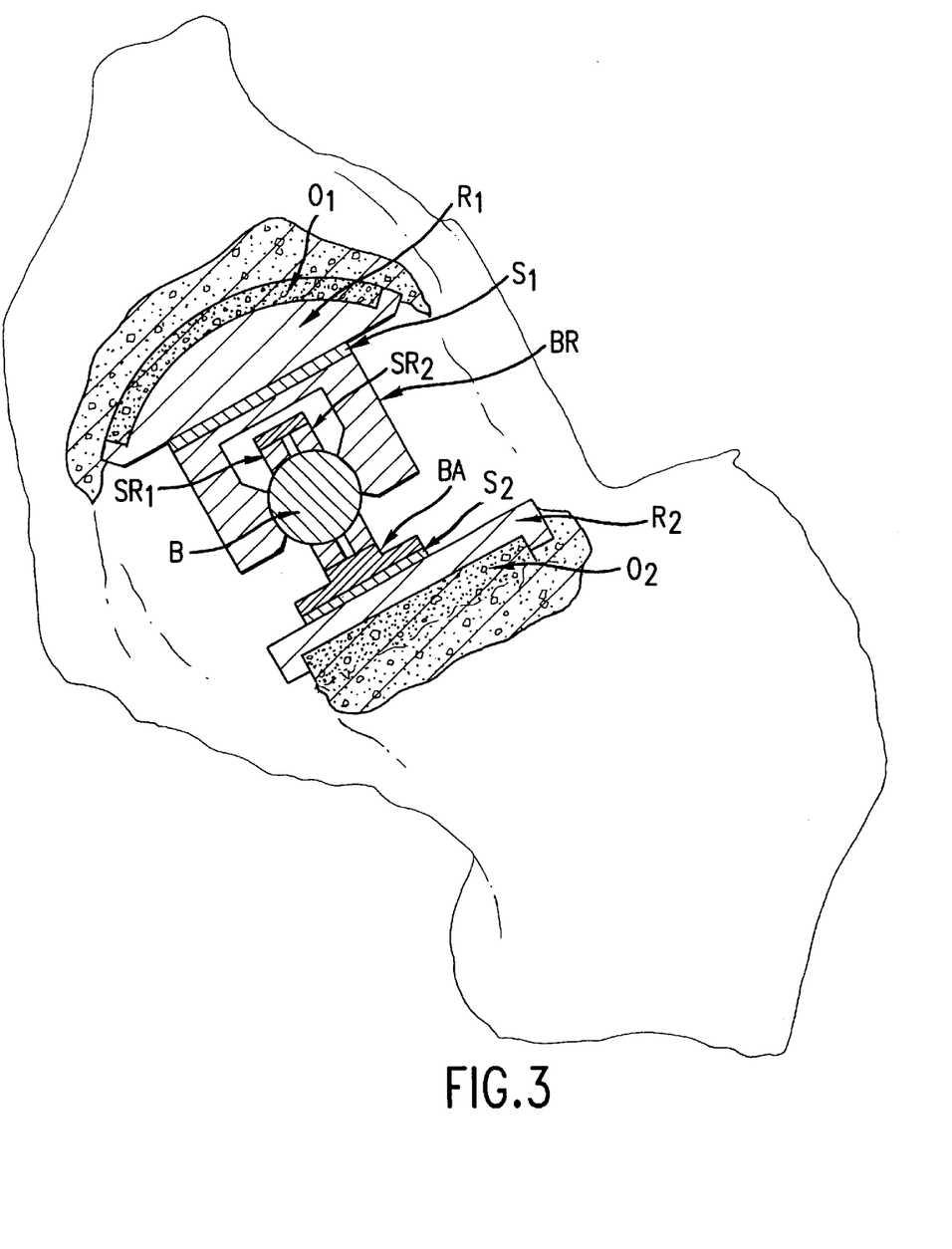
FIG. 3 is a partial sectional view of a total hip prosthesis used in the method of the present invention.
Figures 4A, 4B, 4C:
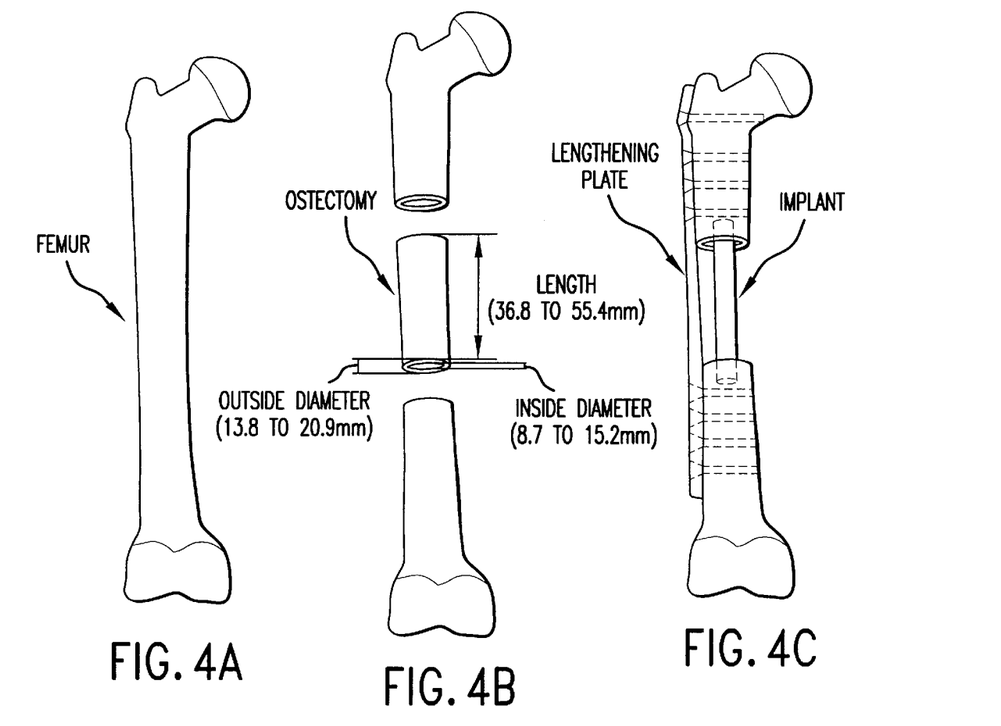
FIGS. 4A, 4B, and 4C are a series of front elevational views of a femur illustrating a surgical procedure used in the present invention.
Figure 4D:
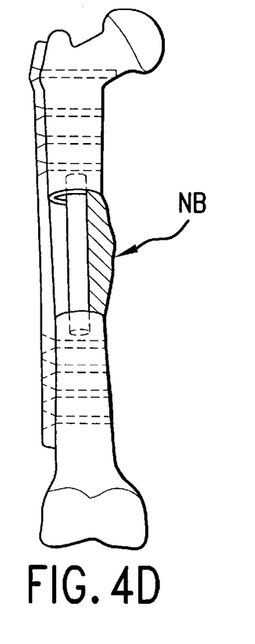
FIGS. 4D, 4E, and 4F are a series of front elevational views corresponding to FIG. 4C showing the new bone at 10 weeks and 35 weeks after surgery, and at 35 weeks after removal of the bone plate.
Figure 4E:
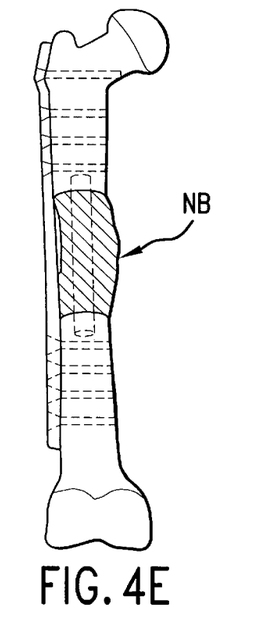
Figure 4F:
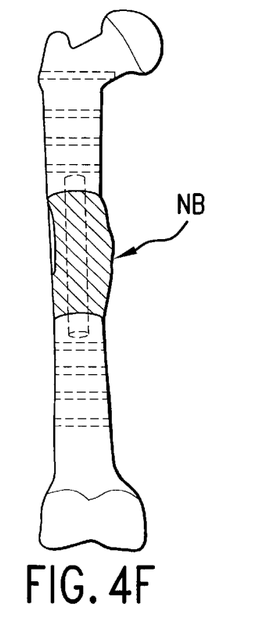
Figure 5:
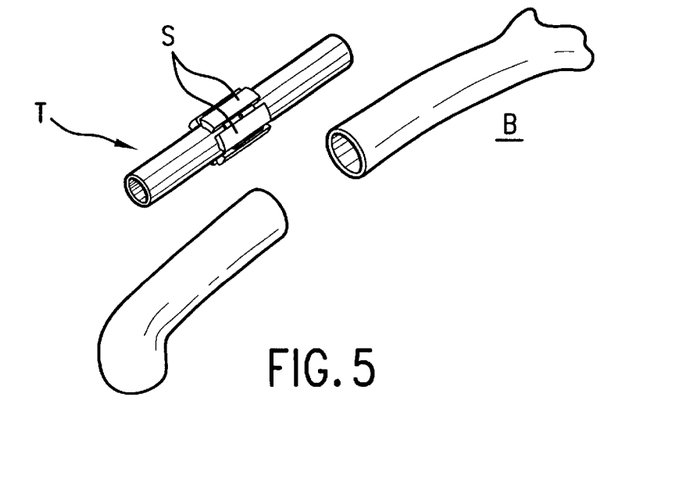
FIG. 5 is a perspective view of a combination guide tube and spacers for reconstruction of the humerus of an avian.

The hip prosthesis shown in FIG. 3 is composed of four components: a sapphire ball and ring assembly, an osteoceramic tissue contact material, a metal body that holds the bearing rings and the osteoceramic in place, and a cage to prevent dislocation. The body includes members to allow adjustment of position and angle, and is in two parts, an acetabular part and a femoral part. The acetabular part provides for adjustment of the angle and thickness of the prosthesis. The femoral part has provision for a femoral stem extension that can be used if necessary. These components are discussed in turn.

The sapphire ball and ring assembly makes up the low-friction ball-and-cup portion of the prosthesis. It is composed of a sapphire ball and two sapphire rings. Sapphire is single-crystal aluminum oxide. It is harder and stronger than polycrystalline aluminum oxide. It is chosen for its low friction and high strength because this makes it possible to use a much smaller ball than is possible with conventional ceramics. Because the ball is smaller it does not require as much space, and this makes it possible to replace the hip without removing much tissue. It fits into the area previously occupied by the femur ball and acetabulum, with provision that the center of rotation of the sapphire ball and ring is at the center of rotation of the joint being replaced. Another advantage of the sapphire ball and ring is that it can be made by inexpensive methods. Sapphire is inexpensive because it has long been grown and used for precision bearings such as clock and watch bearings. It can be produced as rods and tubes that can be cut to provide stock for balls and rings. Diamond machining to produce the bearing surface in the ring is a simple rotational grinding and polishing operation. Making the ball by automatic grinding and polishing machinery is also a simple grinding and polishing operation. This does not require the expensive, computer-controlled milling and polishing operations required for existing ceramic designs. The presence of two rings allows the bearing surface to accommodate the kinematics of joint rotation with greater freedom and less friction.

The osteoceramic tissue contact material is a great improvement over conventional prostheses because bone will bond to it, regenerating to hold it stable and prevent loosening. It is a brittle material that will fail if excessive tensile stresses are imposed. Therefore, it is employed in a way to minimize tensile stresses. It is shaped to, 1.) provide projections, holes, notches or grooves, or combinations thereof, for bone to grow into and prevent movement. Provision for mechanical fixation is also provided, but the holes, notches or grooves may be provided with a key shape so that, once filled, the bone cannot be easily withdrawn. This provides tensile and rotational stability in addition to compressive stability. The osteoceramic is made as dense and strong as possible, but provision is made on the surface to have its surface structure similar to that of the bone it is attached to. In that way the normal physiological responses of the tissue can be used by the body to bond to the implant.

Referring to FIG. 3, the metal body of the acetabular component $R_1$ holds and supports the acetabular osteoceramic $O_1$. The osteoceramic $O_1$ can be pre-stressed with the metal body $R_1$. The surface of the acetabulum is prepared by the surgeon to fit the proximal surface of the osteoceramic $O_1$. The surface of the osteoceramic contains key ways into which the bone of the acetabulum can grow and fix the implant in place. Bone screws through the acetabular body component $R_1$ and the osteoceramic $O_1$ are not shown. Variations in geometry of the tissue contact surface to accommodate acetabular geometry are within the scope of this invention. Shims, $S_1$ can be flat or tapered to adjust the center of rotation of the artificial joint to its desired position. Fixed to the acetabular metal body $R_1$ is the sapphire bearing retainer BR that holds the sapphire ball bearing B in fixed position. The bearing B is held so that it cannot escape. Drilling a hole in the bearing and adding a bolt through the bearing into the two halves of the bearing retainer BR is also within the scope of this patent. The bearing retainer BR is relieved above and below the ball to provide for motion on an axis perpendicular to the plane of the drawing.

Riding on the ball is a sapphire ring bearing assembly BA. It consists of a retainer that surrounds the two sapphire bearing rings that ride on the sapphire ball B. The sapphire bearing rings, $SR_1$ and $SR_2$, are polished to ride freely on the sapphire ball, so that rotation about the horizontal axis in the plane of FIG. 3 is unrestricted. Modest rotation on the vertical axis in the plane of FIG. 3 is also possible, so the artificial joint has the same degrees of freedom as natural hip joint, e.g. abduction=40°. The bearing retainer accepts polished sapphire bearing rings, one medial ($SR_1$) and one lateral ($SR_2$) to the ball, with adjusting mechanisms so that they can be fastened firmly in place when the surgeon assembles the joint.

The bearing assembly BA is fastened to the femoral metal body component $R_2$. Shims, $S_2$ of appropriate shape are provided to adjust the position of the femur to the center of rotation fixed by the position of the ball B.

The femoral metal body component $R_2$ supports the osteoceramic $O_2$ in contact with the bone of the femur. The component $R_2$ can prestress the osteoceramic $O_2$ and it retains it in contact with the bone. Bone screws, not shown, provide for initial fixation of both the femoral metal body component $R_2$ and the osteoceramic $O_2$. The osteoceramic $O_2$ has surface features at the tissue interface to enhance fixation, such as projections similar to the structure of the bone which it contacts. Variations in geometry to accommodate femoral tissue structure are within the scope of this invention. A femoral intramedullary extension is also within the scope of this invention.

The combined assembly BR, B, BA forms a cage which physically prevents dislocation of this artificial joint. Modifications of the geometry to improve this cage-like structure are possible and are included within the scope of this invention.

The femoral component of the metal body part has provision for several different situations. In the case of an arthritic hip with strong, healthy ball and stem it is the articulating surfaces that must be replaced. Because of the small size of the sapphire ball and ring assembly it is possible to not remove the ball and stem of the femur. Only the proximal surface of ball must be removed. It is reamed in a frustrum of a cone configuration so that the femoral osteoceramic component can be recessed into the head of the ball, retaining the strong cortical exterior of the ball to support it. The femoral body part has a component that has a recess to hold the osteoceramic component, providing radial containment. It can be pre-stressed to strengthen the osteoceramic. The proximal portion of the femoral body part supports the sapphire ring assembly. Provision is made for bone screws for fixation. Additional components for displacement and angular adjustment may be provided but are usually not required. In application the surgeon cuts and reams the femoral ball for the femoral osteoceramic and assembles the sapphire ring. (A metal jig with a metal ball fixed in place is used first for testing kinematic alignment.) The acetabular osteoceramic component is fixed in place and the necessary extensions and angular adjustments are made to bring the acetabular sapphire ball into position. Then the femoral jig is removed and the ring-bearing body component is fixed in place. Because the metal body components can be freely chosen this gives the surgeon great flexibility and ease in placing the osteoceramic components and still meet the kinematic and positional requirements.

The surgeon removes the ligament at the head of the ball temporarily. After the prosthesis is in place, the surgeon reattaches the ligament to the femoral head at a position to provide blood to the oriented trabecula supporting the medial aspect of the femoral head.

If the stem of the femur is not strong or if it is fractured it can be cut off and a conventional stem inserted into the medulla of the femur similar to current practice of replacing the stem and head. However, the osteoceramic can be used as the tissue interface material, being supported by the stem assembly.

All such modifications for the support of the femoral component of the sapphire ring are included within the scope of this disclosure.

The joint should not provide electrical contact between the acetabular and femoral body parts.

EXAMPLE 3

The following example discloses a new method for orthopedic surgeons to make bone grafts with artificial sterile material and cause the bone to reunite and repair itself. I have discovered a way to do this, and provide a new method for orthopedic surgeons to make bone grafts with artificial sterile material and cause the bone to reunite and repair itself.

This new method of bone grafting includes a bone grafting material. However, the net result is a graft in which the strength is provided primarily by the natural bone itself, instead of by the graft. The graft is primarily non-loadbearing, although as will be explained later it does participate in mechanical loading during the healing process. The graft serves as a guide for the bone repair and remodeling process to control the macrostructure of the bone response in accordance with the known microstructure physiological repair mechanisms of the tissue. In the end result the bone graft may carry some mechanical load if the tissue response and the bone rebuilding incorporates some of its strength to the final, remodeled bone morphology. Whether or not it carries appreciable load will depend on the geometry at the implant site and the physiological repair responses of the bone itself. The graft has the function of guiding, or directing bone re-growth to restore natural bone.

Natural bone repair requires stabilization and vascularization. The source of blood supply after the initial hematoma and fibrous callous formation is internal through arterial structures and external, from surrounding soft tissue, especially muscles. This blood is conducted in the healing process through the endosteum and periosteum tissues. The periosteum is often stripped in providing access to the bone for internal stabilization and is often injured in the original fracture and post fracture manipulations. If those do not regenerate, but join to themselves at the proximal end and at the distal ends of the remaining bone, non-union occurs. This produces rounded ends enclosing cancellous bone, a typical non-union. Applicant has discovered that these tissues can be guided if a calcium phosphate containing graft is provided so that the periosteum is prevented from joining around the periphery of the bone ends. By using a ceramic graft containing calcium phosphate the rate of bone repair is enhanced and a fibrous capsule is prevented. This is critical to the success of my method. The bone healing, in effect, follows the exterior surfaces of the implant. Although calcium phosphates have been recognized as osteoconductive, and although the idea of a scaffold is not new, no one has recognized the importance of combining these features with the other features disclosed here. And no one has ever succeeded in producing a calcium phosphate implant where bone was induced to repair itself in load-bearing bone-graft situations.

It has long been know that the structure of bone is determined by the loads applied, and that bone remodels to support loads (Wulff's law). Internal fixation, such as a bone plate with screws, is often needed for a bone graft. When a plate is used the rigidity of the plate prevents micromotion adjacent to it. Opposite the plate, because of bending under load micromotion (microstrain) increases, proportional to the distance away from the stabilizing plates. Microstrain excites the physiological responses, such as proliferation of osteoblasts, that are needed for bone generation. This must be controlled for a bone graft to be successful. A gradual transfer of mechanical load from the bone plate to the new bone must be accomplished. If the graft is in a proper position it may be incorporated into the new bone to carry part of the mechanical load. New bone is wavy in structure. It later remodels to mature bone of structure appropriate to the structure of the surrounding bone. During and after the transition the graft may or may not carry load if the supporting bone is strong enough. Ultimately, a successful graft will have remodeled bone suitable to the strength required by the loads imposed. Note that this remodeling will shift the load from the bone plate to the remodeled bone. Ultimately the bone plate can be removed.

The vascular system needed for bone repair must be provided in the design of the graft and its stabilization. Bone cannot regenerate or remodel if this is not done.

This point is illustrated with the following example. A length of bone two and one half times the diameter was removed from the diaphysis of a dog's femur. A tubular bone graft made from a composite ceramic, 50% calcium phosphate and 50% spinel, was inserted in the medullar space, extending into the proximal and distal medulla of the adjacent bone ends; and a bone plate and screws was used to stabilize the bone. The screws holding the plate also restricted the axial displacement of the graft. (FIG. 4) The tube was enclosed by a massive hematoma that became fibrous and immobilized the free-floating bone graft within about 24 hours. There was sufficient space between the endosteum and the implant so that vascularization of the endosteum from the medulla was possible. Regeneration of blood and nerves through the axial core of the tube was also possible so that blood could be supplied to the endosteum at both ends of the graft. Note that radial holes connecting the axial core space with the outer surface of the graft could be provided if necessary. The exterior of the callous and the re-generation of the periosteum was provided with blood supply from the surrounding muscle. The periosteum at the proximal and distal ends of the ostectomy could not close on itself and produce hemispherical ends to the proximal and distal bone because the bone graft is interposed.

Bone regeneration was followed radiologically. After ten weeks bone was visible medially by radiograph. Where microstrain occurred the bone mineralized, as the result of the calcium and phosphate ions released by the implant, and as a result of the micromotion. Over the next few weeks the new bone increased in density and extent until it encapsulated the tubular graft. The tissue gradually accepted more and more of the loads imposed by standing, walking and jumping as it became stronger and more movement. After 35 weeks the bone plate was removed. Further remodeling occurred with time allowing the regenerated and remodeled bone to bridge the gap and provide strength. The graft does not need to be strong enough to support the limb, nor provide much strength after the remodeling is complete. Note that other configurations containing calcium phosphate could be used and are included in the scope of this invention. Note also that the shape of the graft must be designed in such a way as to provide the requirements of bone stress level, physiological responses (vascularity, barrier to endosteal or periosteal joining) rigidity and micromotion and chemical composition (release of $Ca^{2+}$ and $PO_4^{3-}$ ions).

EXAMPLE 4

Members of the Avian class have skeletal features different from mammals because the Avian's fly. All bones are thin-walled. The skeleton is fragile and many of the bones are hollow. Birds like cranes, swans, hawks and eagles often suffer fracture of the humerus. Because the humerus is hollow little endosteal blood supply is available. The vascularity of the external soft tissue is limited, so these fractures heal slowly. The hollow nature makes it difficult to stabilize the fracture with an intermedullary nail. If metallic bone plates are used for stabilization the wing is too heavy so the bird can no longer fly.

Broken wings are often compound fractures with bone ends exposed. These are usually necrotic, so the ends proximal and distal to the fracture must be removed.

The method of bone reconstruction can be applied here: The osteoceramic can be used to stabilize the fracture and induce bone bonding. Its calcium phosphate nature enhances bone healing and callous formation and mineralization. A thin-walled tube no larger in thickness than the humerus wall is chosen of length sufficient to stabilize the fracture with an outside diameter just large enough to enter the open medulla of the proximal and distal bone. If necessary a spacer of osteoceramic can be placed over the stabilizing tube, its length chosen to separate the proximal and distal ends of the bone to give the same length as the bone in the contralateral wing. It can be cemented or sutured in place on the osteoceramic stabilizing tube. The wall thickness of the spacer need only be thick enough to prevent the bone ends from sliding on the stabilizing tube. The fit of the stabilizing tube is critical. A selection of tubes of various diameters need to be available. However, because of curvature and non-circularity of the bone a suitable diameter can be selected and cut to length. The surgeon stabilizes the fracture as described above and sutures the soft tissue to provide good vascular content with the original periosteum.

In this example, the osteoceramic has been used; the fracture has been bridged by the implant; the fracture has been stabilized; the geometry of the implant and its structure is the same as the adjacent bone, and the vascularity coming only external to the bone and implant assembly has been accommodated. The stress level in the bone at the fracture site is within the range normally found in the bone. The tissue can repair itself bonding to the implant. By judicious selection of wall thickness and stabilizing tube length the bird will be able to fly when the bone remodelling is sufficient. Note that this example also provides a barrier for the healing periosteum to prevent closure on itself at the proximal and distal ends of the bone fracture. Note also that rotation on the longitudinal axis must be prevented during stabilization. The surgeon can prevent rotation by stabilizing tube fit or fixation with sutures engaging holes or notches in the tube ends.

Thus, it can be seen that at least all of the stated objectives have been achieved.

Obviously, many modifications and variations of the present invention are possible in light of the above teachings. It is therefore to be understood that, with in the scope of the appended claims, the invention may be practiced otherwise than as specifically described.

APPENDIX

1. Mow, V. C., Roth, V., and Armstrong, C. G., Biomechanics of joint cartilage, in *Basic Biomechanics of the Skeletal System* (Frankel, V. H., and Nordin, M., eds.), Lea and Febiger, Philadelphia, 1980.
2. Wolff, J. L., *Das Gesetz der Transformation of Knochen*, A. Hirschwald, Berlin 1892.
3. Cowin, S. C., VanBurshirk, W. C., and Ashman, R. B., Properties of bone in *Handbook of Bioengineering* (Skalak, R., and Chien, S., eds.), McGraw-Hill, New York, 1982.
4. Bouvier, M., The biology and composition of bone, in *Bone Mechanics* (Cowin, S. C., ed.), CRC Press, Boca Raton, Fla., 1989.
5. Hargest, T. E., Gay, C. V., Scharer, H., and Wasserman, A. J., Vertical distribution of cells and matrix of epiphyseal grow plate cartilage determined by quantitative electron probe analysis, *J. Histochem. Cytochem.*, 4(33), 275 1985.
6. Glimcher, M. J., Composition, structure and organization of bone and other mineralized tissues and the mechanism of calcification, in *Handbook of Physiology*, Vol. 7, American Physiology Society, Washington, D.C., 1976.
7. von Recum, A. F. (ed.), *Handbook of Biomaterials Evaluation*, Macmillan, New York, 1986.
8. Ducheyne, P., Martens, M., Aernocedt, E., Mulier, J., and DeMeester, P., Skeletal fixation by metal fiber coating of the implant, *Acta Orthop.*
9. Grenoble, D. E., and Voss, D., Materials and designs for implant dentistry, *Biomed Mater. Devices Artif. Organs*, 4, 133, 1976.
10. Bokros, J. C., Carbon biomedical devices, *Carbons*, 15, 355, 1977.
11. Kay, J. F., Bioactive surface coatings for hard tissue biomaterials, *Handbook of Bioactive Ceramnics*, Vol, 2 (Yamamuro, T., Hench., L. L., and Wilson, J. eds.), CRC Press, Boca Raton, Fla., 1990.

12. Spector, M., Harmon, S. L. and Dreutner, A., Characteristics of tissue ingrowth into proplast and porous polyethylene implants in bone, *J. Biomed. Mater. Res.*, 13, 672, 1979.
13. Brunsky, J. B., Implants: Biomaterials and biomechanics, *J. Cal. Den. Assoc.*, 16, 66, 1988.
14. Brunsky, J. B., Biomechanical factors affecting the bone dental implant interface, *Clin. Mater.*, 10, 153, 1992.
15. Didisheim, P., Dewanjee, M. K., Kaye, M. P., et al., Nonpredictability of long-term in vivo response from short-term in vitro or ex vitro blood-material interactions., *Trans. Am. Soc. Artif. Intern. Org.*, 30, 370, 1984.
16. Hulbert, S. F., Levine, S. N., and Moyle, D. D., *Prosthesis and Tissue: The Interfacial Problems*, Wiley, New York, 1974.
17. Park, J. B., and Lakes, R. S., Tissue response to implants, in *Biomaterials: An Introduction*, 2nd ed., Plenum Press, New York, 1992, Chap. 10.
18. Ref. 17, Chap. 5.
19. Yamada, H., in *Strength of Biological Materials* (Evans, F. G., ed.), Williams & Wilkins. Baltimore, 1970.
20. Clark, C., Dorlot, J. M., Graham, J., Levine, D. J., Oonishi, H., Rieu, J., Rigney, D., Schwartz, G., Sedel, L., Tonie, As. and Zitelli, J., Biomechanical stability and design, wear, *Ann. NY Acad. Sci.*, 23, 292–296, 1988.
21. deGroot, K. (ed.), *Bioceranics of Calcium Phosphate*, CRC Press, Boca Raton, Fla. 1983.
22. deGroot, K., Dental implants, in *Bioceramics of Calcium Phosphates* (deGroot, K., ed.), CRC Press, Boca Raton, Fla., 1983.
23. Aksaci, D., Evaluation of a fluorapatite-spinel ceramic as a bone implant, Ph.D. Thesis, Iowa State University, 1981.
24. Park, J. B. and Lakes, R. S., Hard tissue replacement, ii, in *Biomaterials: An Introduction*, 2nd ed., Plenum Press, New York, 1992, Chap. 11.
25. Janikowski, T., and McGee, T. D., Tooth roots for permanent implantation. *Proc. Iowa Acad. Sci.* 76, 1969, p. 113.
26. McGee, T. D., and Wood, J. L., Calcium phosphate osteoceramics, *J. Biomed. Mater. Res. Synmposiuim*, 5(Pt.I), 137, 1974.

What is claimed is:

1. A permanent joint replacement device for articulably connecting a first and a second bone, comprising:
    a sapphire ball;
    a first sapphire ring contacting said sapphire ball and permitting relative movement of said sapphire ball therewithin;
    a first retainer for holding said first sapphire ring;
    a first osteoceramic body attached to said first retainer and having a first bone contact surface thereon;
    a second sapphire ring contacting said sapphire ball and permitting relative movement of said sapphire ball therewithin;
    a second retainer for holding said second sapphire ring; and
    a second osteoceramic body attached to said second retainer and having a second bone contact surface thereon.

2. The joint replacement device of claim 1, wherein said first retainer comprises a metal cup.

3. The joint replacement device of claim 1, wherein said first retainer further comprises an adjustable component.

4. The joint replacement device of claim 1, wherein at least one of the first and the second bone contact surfaces further comprises a plurality of indentations thereon.

5. The joint replacement device of claim 4, wherein the plurality of indentations are selected from the group consisting of grooves, holes, and notches.

6. The joint replacement device of claim 4, wherein the plurality of indentations are tapered.

7. The joint replacement device of claim 6, wherein the plurality of indentations are outwardly tapered so that they are narrowest at an outermost edge.

8. The joint replacement device of claim 1, wherein at least one of the first and the second bone contact surfaces further comprises a plurality of projections thereon.

9. The joint replacement device of claim 8, wherein the plurality of projections are tapered.

10. The joint replacement device of claim 9, wherein the plurality of projections are inwardly tapered so that they are widest at an outermost edge.

11. The joint replacement device of claim 1, wherein said second retainer comprises a metal post.

12. The joint replacement device of claim 1, wherein said second retainer further comprises an adjustable component.

13. The joint replacement device of claim 1, further comprising means for attaching said first osteoceramic body to the first bone.

14. The joint replacement device of claim 13, wherein said means are screws.

15. The joint replacement device of claim 1, wherein said second osteoceramic body further comprises an intramedullary extension adapted to fit within a medullary cavity of the second bone.

16. The joint replacement device of claim 1, further comprising means for attaching said second osteoceramic body to the second bone.

17. The joint replacement device of claim 16, wherein said means are screws.

18. The joint replacement device of claim 1, further comprising a bolt extending through said sapphire ball.

19. A permanent bone replacement device for connecting to a portion of damaged bone, comprising:
    an osteoceramic material formed into a hollow cylinder having an outer surface, a first end and a second end;
    a plurality of notches in at least one of the first and the second ends; and
    a plurality of web-like projections on the outer surface.

20. The bone replacement device of claim 19 wherein the osteoceramic material has a plurality of perforations.

21. The bone replacement device of claim 20, wherein at least some of the plurality of perforations have a diameter of at least 200 microns.

22. The bone replacement device of claim 19, further comprising means for stabilizing said osteoceramic material relative to the damaged bone.

23. The bone replacement device of claim 22, wherein said means for stabilizing said osteoceramic material comprises a plate and screws, wherein said plate is attached to said osteoceramic material, and said screws connect said plate to the damaged bone.

24. The bone replacement device of claim 19, wherein said osteoceramic material comprises at least 25 percent by volume of a calcium-phosphate component.

25. The bone replacement device of claim 24, wherein said osteoceramic material comprises about 50 percent by volume of the calcium-phosphate component.

26. The bone replacement device of claim 24, wherein the calcium-phosphate component has a calcium to phosphate ratio within the range of about 1.5 to 1.67.

27. The bone replacement device of claim 24, wherein the calcium-phosphate component is selected from the group consisting of tricalcium phosphate, hydroxyapatite, oxyapatite, and fluorapatite.

28. A permanent bone replacement device for connecting to a portion of damaged bone, comprising:
   an osteoceramic material formed into a hollow cylinder having an outer surface, a first end and a second end;
   a plurality of notches in at least one of the first and the second ends; and
   wherein said plurality of notches are tapered.

29. The bone replacement device of claim 28, wherein said plurality of notches are outwardly tapered so that they are narrowest at an outermost edge of said cylinder.

30. A permanent bone replacement device for connecting to a portion of damaged bone, comprising:
   an osteoceramic material formed into a hollow cylinder having an outer surface, a first end and a second end;
   a plurality of notches in at least one of the first and the second ends; and
   a plurality of longitudinal grooves in the outer surface.

31. The bone replacement device of claim 30, wherein said plurality of longitudinal grooves extend substantially along an entire length of the cylinder.

32. The bone replacement device of claim 31, wherein said plurality of longitudinal grooves are tapered.

33. The bone replacement device of claim 32, wherein said plurality of longitudinal grooves are outwardly tapered so that they are narrowest at an outermost portion of the outer surface.

34. The bone replacement device of claim 30, wherein said plurality of notches are radially aligned with said plurality of longitudinal grooves to form a plurality of notched grooves in the outer surface.

35. The bone replacement device of claim 30, further comprising a plurality of perforations located in said plurality of longitudinal grooves.

36. A permanent bone replacement device for connecting first and second portions of damaged bone, comprising:
   an osteoceramic tube having an outer surface, a first end and a second end, wherein the osteoceramic comprises about 50 percent by volume of a calcium-phosphate component; and
   a plurality of notches in the first and the second ends, wherein said plurality of notches are outwardly tapered so that they are narrowest at an outermost edge of said tube.

37. The bone replacement device of claim 36, further comprising a plurality of longitudinal grooves in the outer surface, and a plurality of perforations in said tube, wherein said plurality of perforations have a diameter of at least 200 microns.

38. The bone replacement device of claim 37, wherein said plurality of perforations are located in said plurality of longitudinal grooves.

39. The bone replacement device of claim 37, wherein said plurality of longitudinal grooves are outwardly tapered so that they are narrowest at an outermost portion of the outer surface of said tube.

40. The bone replacement device of claim 37, wherein said plurality of notches are radically aligned with said plurality of longitudinal grooves to form a plurality of notched grooves in the outer surface.

* * * * *